(12) United States Patent
Kinoshita et al.

(10) Patent No.: US 7,018,795 B2
(45) Date of Patent: Mar. 28, 2006

(54) HYBRIDIZATION PROBE AND TARGET NUCLEIC ACID DETECTING KIT, TARGET NUCLEIC ACID DETECTING APPARATUS AND TARGET NUCLEIC ACID DETECTING METHOD USING THE SAME

(75) Inventors: Takatoshi Kinoshita, Aichi (JP); Shintaro Washizu, Shizuoka (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 169 days.

(21) Appl. No.: 10/103,830

(22) Filed: Mar. 25, 2002

(65) Prior Publication Data

US 2002/0168666 A1 Nov. 14, 2002

(30) Foreign Application Priority Data

Mar. 23, 2001 (JP) .......................................... 2001-86306

(51) Int. Cl.
C12Q 1/68 (2006.01)
C07H 21/02 (2006.01)

(52) U.S. Cl. ......................... 435/6; 536/23.1; 536/24.3; 536/24.31; 536/24.33
(58) Field of Classification Search ..................... 435/6; 536/23.1, 24.3, 24.31, 24.33
See application file for complete search history.

(56) References Cited

U.S. PATENT DOCUMENTS

| | | | |
|---|---|---|---|
| 4,350,761 A | | 9/1982 | Yamamoto |
| 4,810,639 A | | 3/1989 | Pankratz |
| 4,868,105 A | * | 9/1989 | Urdea ............................ 435/6 |
| 4,909,990 A | | 3/1990 | Block et al. |
| 5,281,539 A | | 1/1994 | Schramm |
| 5,766,784 A | * | 6/1998 | Baskaran et al. ............ 428/702 |
| 5,783,392 A | * | 7/1998 | Seibl et al. ...................... 435/6 |
| 5,800,994 A | * | 9/1998 | Martinelli ...................... 435/6 |
| 6,083,689 A | | 7/2000 | Martinelli et al. |
| 6,238,864 B1 | | 5/2001 | Yan |
| 6,686,150 B1 | * | 2/2004 | Blackburn et al. ............. 435/6 |

OTHER PUBLICATIONS

Baril et al, "Chromatography of ribonuclease treated myosin extracts from early embryonic chick muscle", Science (1964) 146:413–414.*

Liu, et al., "Cell–ELISA using B–galactosidase conjugated antibodies" Journal of Immunological Methods 234 (Feb. 2000) p. 153–167).

Doi, et al., "The control of structure and functions of lb–film composed of bio–related polymers." First International Symposium on Biomimetic Materials Processing. Jan. 11, 2001, p. 19.

Kinoshita, et al., "Preparation of a structual color forming system by polypeptide–based lb films." The fourth NIMC International Symposium on Photoreaction Control and Photofunctional Materials. Mar. 14, 2001, pp. 1–91–1–12.

Yokoi, et al., "Nano–phase Separation in the Monolayer Composed of α–Helical Copolypeptide at Air/Water Interface." Chemistry Letters 2000. Jul. 13, 2000, pp. 1210–1211. The chemical Society of Japan.

Mouri, et al., "The molecular recognition and polypeptide orientation in the monolayer at oil/water interface." 12$^{th}$ Academic Symposium of MRS Japan manuscripts. Dec. 7, 2000, p. 66.

Hosokawa, et al., "The molecular orientation of a peptide–based amphiphile at hexane/water interface." Chemistry Letters 1997. Apr. 9, 1997, pp. 745–746. The Chemical Society of Japan.

Kinoshita, et al., "The guest–induced oscillation of a monolayer composed of polypeptide containing β–cyclodextrin at the termina.." Choas, vol. 9, No. 2, Jan. 19, 1999, pp. 276–282.

T. Kinoshita, "Control of Superfine Structure of Membrane and Their Characterization," *Polymer*, (Sep., 1991), vol. 50, pp. 648–651.

T. Kawaguchi, et al., "A Device for Visual Detection of Antigens and Antibodies by Means of Light Interference", *Thin Solid Films,* (1990), vol. 191, pp. 369–381.

T. Kinoshita, et al., "Structural Color Forming System Composed of Polypeptide–based LB Films", in *Nanotechnology and Nano–Interface Controlled Electronic Devices,* Tokyo: Elsevier, (2003), pp. 233–252.

T. Miyagi, et al., "Structural Color with Polypeptide LB Film," *Transactions of the Materials Research Society of Japan,* (2002), vol. 27, No. 3, pp. 555–558.

H. Yokoi, et al., "Polypeptide Membranes at an Interface", *Prog. Polym. Sci.,* (2002), pp. 341–357.

Color Tone Control By External Stimuli, Nagoya Institute of Technology, Imitating Function of Bio–skins Applicable to Display Devices, *Nikkan Kogyo Shinbun,* Dec. 28, 2000, Japan.

T. Doi et al., Symposium: Building of Molecular Composition and Its Function, Building and control of peptide type signal transfer function, A506, Nagoya Institute of Technology, Symposium held by JST, Nov. 28, 2000, Japan.

H. Yokoi et al., Preparation of Amphiphilic α–helix LB film, *Polymer Preprints, Japan.* vol. 49 No. 12 IS07, Nagoya Institute of Technology, 2000, Society of Polymer Science, Japan.

(Continued)

*Primary Examiner*—Jeffrey Fredman
(74) *Attorney, Agent, or Firm*—Sughrue Mion, PLLC

(57) ABSTRACT

The present invention relates to a hybridization probe having a rod-shaped boby and nucleic acid which is bonded to the rod-shape material and specifically bonds to a target nucleic acid and also relates to a target nucleic detecting kit, a target nucleic acid detecting apparatus and a target nucleic acid detecting method using the same.

11 Claims, 8 Drawing Sheets

OTHER PUBLICATIONS

H. Yokoi et al., Evaluation of molecular orientation of amphiphilic α–helix water surface monomolecular film, *Polymer Preprints, Japan.* vol. 49 No. 13 lipd090. Nagoya Institute of Technology, 2000, Society of Polymer Science, Japan.

Y. Okahata, Sensing of Odorous and Bitter Substances by using a Bilayer Molecular Film–coated Quartz Oscillator, *Biophysics*, vol. 28, No. 6 Pandect. Tokyo Institute of Technology, 1988, Japan.

Y. Okahata, Prospect for Chemical Information Conversion Membrane, Molecular Recognition to be realized on a Lipid Bilayer Molecular Membrane, *Sen–I Gakkaishi (Fiber and Industry)* vol. 46, No. 2 Feature: Functional Macromolecular Membranes Films, 1990, Japan.

K. Ariga et al., Evaluation of the Viscoelasticity of the Membrane with the Use of a Quartz Oscillator, Phase Transition of the LB film, vol. 28 No. 11, Tokyo Institute of Technology, 1990, Japan.

H. Yokoi et al., *The 48th Symposium on Macromolecules*, The Two Dimensional Orientation Control of Amphiphilic α–helix Molecule, II P f094, Nagoya Institute of Technology, Oct. 6, 1999, Niigata, Japan.

H. Yokoi et al., *The 49th Annual Meeting of the Society of Polymer Science, Japan (SPSJ)*, The pH Dependence of Molecular Orientation in Monolayer Composed of Amphiphilic α–helix Molecule at Air–water Interface, I Pg173, Nagoya Institute of Technology, May 29, 2000, Nagoya, Japan.

H. Yokio et al., *the 49th Symposium on Macromolecules*, Preparation of LB Film consisting of Amphiphilic α–helix Molecule, IS 07, Nagoya Institute of Technology, Sep. 27, 2000, Sendai, Japan.

Y. Nagata, et al., *The 43rd Annual Meeting of the Society of Polymer Science, Japan (SPSI)*, Preparation and Function of Polypeptide Containing a Substrate–binding Site at the Molecular Terminal, II–9–06, Nagoya Institute of Technology, and National Institute of Materials and Chemical Research, Tsuukuba, May 26, 1994, Nagoya, Japan.

H. Yokoi et al., *The 49$^{th}$ Symposium on Macromolecules*. Evaluation of molecular orientation of amphiphilic α–helix water surface monomolecular film, IIPd090, Nagoya Institute of Technology, Sep. 27, 2000, Sendai, Japan.

H. Hosokawa et al., *The 44th Annual Meeting of the Society of Polymer Science, Japan (SPSJ)*, Functional Control of Polypeptide Containing an Inclusion Terminal Group, II Pel 119, May 30, 1995, Yokohama, Japan.

H. Hosokawa et al., Functional Control of Polypeptide Containing an Inclusion Terminal Group, Preprints of Annual meeting of the Society of Fiber Science and Technology, Japan, G–264 3G17, Jun. 29, 1995, Tokyo (Sen–I Gakkai).

H. Hosokawa et al., *45$^{th}$ Annual Meeting of Society of Polymer Science of Japan*. Monolayer of polypeptide containing a cyclodextrin at the terminal. IIIPb100, Nagoya Institute Technology, Nagoya and National Institute of Materials and Chemical Research, Tsukuba, May 29, 1996, Nagoya, Japan.

H. Hosokawa et al., *45$^{th}$ Symposium of Society of Polymer Science of Japan*. Molecular orientation of polypeptide containing a cyclodextrin at the terminal in the monolayer and its function, 2Pb44, Nagoya Institute of Technology, Oct. 2, 1996, Hiroshima, Japan.

H. Hosokawa et al., *46th Annual Meeting of Society of Polymer Science of Japan*, Structural control of polypeptide containing an active site at the terminal in monolayer and its function, IIPb108, Nagoya Institute of Technology, May 24, 1997, Tokyo, Japan.

A. Kato et al., *47th Annual Meeting of Society of Polymer Science of Japan*, Characterization of polypeptide monolayer containing the molecular recognition site, IIIPd124, Nagoya Institute of Technology, May 29, 1998, Kyoto, Japan.

A. Kato et al., *29th Annual Meeting of Union Chemistry–Related Societies in Chubu Area, Japan*, Characterization of polypeptide monolayer containing a cyclodextrin at the terminal, IB0705, Nagoya Institute of Technology, Oct. 3, 1998, Toyohashi, Japan.

H. Yokoi et al., The control of molecular orientation in monolayer of amphiphilic α–helix, *Preprints presented at 15th Symposium of Membrane Science and Technology*, 3PA53, Nagoya Institute of Technology and Core Research for Evolutional Science and Technology, May 12, 1999, Chiba, Japan (Sen–I–Gakkai).

T. Doi et al., *48th Symposium of Society of Polymer Science of Japan*, The molecular orientation and oscillation of polypeptide monolayer at oil/water interface, IIIJ02, Nagoya Institute of Technology and Core Research for Evolutional Science and Technology, Oct. 8, 1999, Niigata, Japan.

T. Doi et al., *Open Symposium of Creation and Functions of New Molecules and Molecular Assemblies sponsored by Core Research for Evolutional Science and Technology (CREST)*, Creation of peptide–type signal transmitting function and control of its function, A506, Nagoya Institute of Technology, Nov. 28, 2000, at Japan Science and Technology Corporation (JST), Tokyo, Japan.

T. Doi, Molecular alignment of poly(γ–methyl–L–glutamate) containing a β–cyclodextrin at the terminal and molecular identification (n–hexane/water interface), *Control of molecuar alignment of polypeptide molecular film* published by Dr. Tomokiyo Doi, chapter 4, 2000.

* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: DNA Synthesizer

<400> SEQUENCE: 1
tataaacttg tggtagttgg acct                                              24

<210> SEQ ID NO 2
<211> LENGTH: 21
<212> TYPE: DNA
<213> ORGANISM: Artificial Sequence
<220> FEATURE:
<223> OTHER INFORMATION: DNA Synthesizer

<400> SEQUENCE: 2
tatcgtcaag gcactcttgc c                                                 21
```

HYBRIDIZATION PROBE AND TARGET NUCLEIC ACID DETECTING KIT, TARGET NUCLEIC ACID DETECTING APPARATUS AND TARGET NUCLEIC ACID DETECTING METHOD USING THE SAME

BACKGROUND OF THE INVENTION

1. Field of the Invention

The present invention relates to a highly sensitive hybridization probe and to a target nucleic acid detecting kit, a target nucleic acid detecting apparatus and a target nucleic acid detecting method using the same.

2. Description of the Related Art

For a method in which a target gene sequence is detected in a nucleic acid polymer or a method in which difference or homology of plural nucleic acid polymers is judged, there has been known a hybridization method in which a single-stranded polymer (DNA or RNA) which is complementary to a partial sequence of the target nucleic acid polymer is used as a probe.

In that hybridization method, a single-stranded target nucleic acid polymer is fixed to a nitrocellulose film or a Nylon film, an aqueous solution of probe nucleic acid labeled with radioisotope or enzyme is added onto the film and, since only hybridized probe nucleic acid polymer remains on the film after being washed with water when the probe nucleic acid polymer is hybridized to the target nucleic acid polymer, radioactivity from the labeled radioisotope of the probe nucleic acid or chemiluminescence or color of precipitate produced by the enzyme is detected whereby it is possible to judge whether a target base sequence is present in the target nucleic acid polymer.

However, in the handling of radioisotopes, a special license or equipment is necessary and that is not for general use. In addition, there is a problem that labeling of a single-stranded probe nucleic acid polymer with enzyme, luminous substance, and the like is expensive, labor-intensive and time-consuming.

In the Japanese Patent Laid-Open No. 210198/1991 for example, there is a description for a method in which a hybrid is formed from DNA which is modified by antigen having a base sequence complementary to the target DNA and then it is made to react with an enzymatically modified antibody to detect the product.

However, there are problems in the method that its quantitative property is poor due to inactivation of the enzymatic activity and that much time is needed for the operation of preparing the enzymatically modified antibody, and the like., the treatment and the measurement.

SUMMARY OF THE INVENTION

Under such circumstances, an object of the present invention is to solve various problems in the past and to achieve the following object.

Thus, an object of the present invention is to provide a hybridization probe by which the reaction for the formation of DNA hybrid may easily and directly be measured and the formation of DNA hybrid may be tested easily and highly precisely and also to provide a target nucleic acid detecting kit, a target nucleic acid detecting apparatus and a target nucleic acid detecting method using the same.

The hybridization probe of the present invention has a rod-shaped body and nucleic acid which is bonded to the rod-shaped body and specifically bonds to a target nucleic acid. As a result thereof, it is now possible to manifest the reaction for the formation of DNA hybrid easily and directly and to test the formation of DNA hybrid easily and highly precisely.

The target nucleic acid detecting kit of the present invention contains a hybridization probe having a rod-shaped body with a length of 810 nm or shorter and nucleic acid which is bonded to the rod-shaped body and specifically bonds to a target nucleic acid and reflects an incident light as colored interference light when aligned in a film-like shape; and any of dish, plate and tube.

The hybridization probe aligned in a film-like shape reflects the incident light as colored interference light on the basis of a multi-layer thin film interference theory which is a basic principle of color formation of the scaly powder of the wings of a Morpho butterfly. When the change in wavelength based on the reflection of the incident light as colored interference light brought out by changes in length or refractive index at the time the film-like hybridization probe hybridizes with a target nucleic acid is measured, the target nucleic acid in the sample may be detected quickly by a simple operation in a reliable manner.

The first embodiment of the target nucleic acid detecting apparatus of the present invention is equipped with a hybridization probe having a rod-shaped body of a length of 810 nm or shorter and nucleic acid which is bonded to the rod-shaped body and bonds to a target nucleic acid and reflecting the incident light as colored interference light when aligned in a film-like shape; a sample adding means n which the hybridization probe is contacted to a sample; and a colored wavelength measuring means in which changes in wavelength by reflection of an incident light as colored interference light of the film-like hybridization probe which is hybridized to the target nucleic acid are measured.

The hybridization probe aligned in a film-like shape reflects incident light as colored interference light on the basis of a multi-layer thin film interference theory which is a basic principle of color formation of the scaly powder of the wings of a Morpho butterfly. When the change in wavelength based on the reflection of the incident light as colored interference light brought out by changes in length or refractive index at the time the film-like hybridization probe hybridizes with a target nucleic acid is measured, the target nucleic acid in the sample may be detected.

The second embodiment of the target nucleic acid detecting apparatus of the present invention is equipped with a biosensor having a rod-shaped body and nucleic acid which is bonded to a hybridization probe having a rod-shaped body and specifically bonds to a target nucleic acid in which an amphiphilic biosensor is aligned on quartz oscillator or surface acoustic wave element in a film-like shape; an oscillation circuit whereby changes in mass or changes in viscoelasticity when a target nucleic acid is hybridized to the biosensor are oscillated as frequency; and a frequency counter whereby frequency of the oscillation oscillated from the oscillation circuit is measured.

As a result, changes in mass or changes in viscoelasticity when the hybridization probe of the biosensor hybridized the target nucleic acid may be detected as a frequency with a high sensitivity and within a short time.

The target nucleic acid detecting method according to the present invention comprises a contacting step in which a hybridization probe having a rod-shaped body of a length of 810 nm or shorter, having nucleic acid which is bonded to the rod-shaped body and specifically bonds to a target nucleic acid, reflecting the incident light as colored interference light when aligned in a film-like shape and being amphiphilic with a sample and a wavelength measuring step in which changes in wavelength based on reflection of an incident light as colored interference light of film-like hybridization probe hybridized to the target nucleic acid are measured.

The hybridization probe aligned in a film-like shape reflects the incident light as colored interference light on the basis of a multi-layer thin film interference theory which is a basic principle of color formation of the scaly powder of the wings of a Morpho butterfly. When the change in wavelength based on the reflection of the incident light as colored interference light brought out by changes in length or refractive index at the time the film-like hybridization probe hybridizes with a target nucleic acid is measured, the target nucleic acid in the sample may be detected efficiently by a simple operation in a reliable manner.

BRIEF DESCRIPTION OF THE DRAWINGS

FIGS. 7A and 7B is an example view of a quartz oscillator in which FIG. 7A is a plan view and FIG. 7B is a front view.

DESCRIPTION OF THE PREFERRED EMBODIMENTS

Hereinafter, the present invention will be described in more detail.

Figure 1:
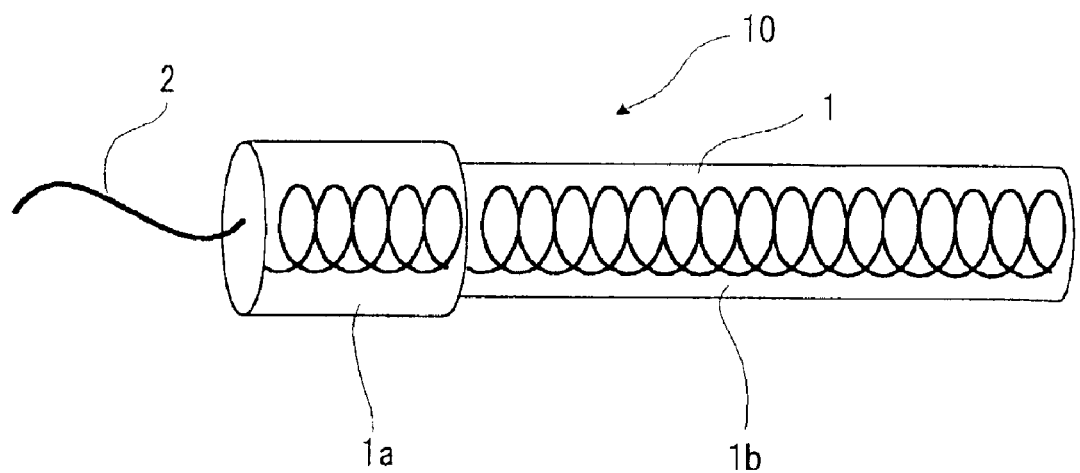
FIG. 1 is a schematic view of a hybridization probe relating to one example of the present invention.

As shown in FIG. 1 as an example, the hybridization probe 10 of the present invention has a rod-shaped body 1 and nucleic acid 2 which is bonded to the rod-shaped body 1 and specifically bonds to a target nucleic acid. Incidentally, the exemplary hybridization probe 10 of FIG. 1 is an amphiphilic polypeptide of an α-helix structure in which the part 1$a$ of the rod-shaped body is hydrophobic while the part 1$b$ thereof is hydrophilic.

<Rod-Shaped Body>

The rod-shaped body is not particularly limited provided that it is rod-shaped, and may be appropriately selected in accordance with the object. The rod-shaped body may be either a rod-shaped inorganic substance or rod-shaped organic substance, but a rod-shaped organic substance is preferable.

Examples of rod-shaped organic substances are biopolymers, polysaccharides, and the like.

Suitable examples of biopolymers are fibrous proteins, α-helix polypeptides, nucleic acids (DNA, RNA), and the like. Examples of fibrous proteins are fibrous proteins having α-helix structures such as α-keratin, myosin, epidermin, fibrinogen, tropomyosin, silk fibroin, and the like. Suitable examples of polysaccharides are amylose and the like.

Among rod-shaped organic substances, spiral organic molecules whose molecules have a spiral structure are preferable from the standpoints of stable maintenance of the rod shape and internal intercalatability of other substances in accordance with an object. Among the aforementioned substances, those with spiral organic molecules include α-helix polypeptides, DNA, amylose, and the like.

{α-Helix Polypeptides}

α-helix polypeptides are referred to one of secondary structures of polypeptides. The polypeptide rotates one time (forms one spiral) for each amino acid 3.6 residue, and a hydrogen bond, which is substantially parallel to the axis of the helix, is formed between a carbonyl group (—CO—) and an imide group (—NH—) of each fourth amino acid, and this structure is repeated in units of seven amino acids. In this way, the α-helix polypeptide has a structure which is stable energy-wise.

The direction of the spiral of the α-helix polypeptide is not particularly limited, and may be either wound right or wound left. Note that, in nature, only structures whose direction of spiral is wound right exist from the standpoint of stability.

The amino acids which form the α-helix polypeptide are not particularly limited provided that an α-helix structure can be formed, and can be appropriately selected in accordance with the object. However, amino acids which facilitate formation of the α-helix structure are preferable. Suitable examples of such amino acids are aspartic acid (Asp), glutamic acid (Glu), arginine (Arg), lysine (Lys), histidine (His), asparagine (Asn), glutamine (Gln), serine (Ser), threonine (Thr), alanine (Ala), valine (Val), leucine (Leu), isoleucine (Ile), cysteine (Cys), methionine (Met), tyrosine (Tyr), phenylalanine (Phe), tryptophan (Trp), and the like. A single one of these amino acids may be used alone, or two or more may be used in combination.

By appropriately selecting the amino acid, the property of the α-helix polypeptide can be changed to any of hydrophilic, hydrophobic, and amphiphilic. In the case in which the α-helix polypeptide is to be made to be hydrophilic, suitable examples of the amino acid are serine (Ser), threonine (Thr), aspartic acid (Asp), glutamic acid (Glu), arginine (Arg), lysine (Lys), asparagine (Asn), glutamine (Gln), and the like. In the case in which the α-helix polypeptide is to be made to be hydrophobic, suitable examples of the amino acid are phenylalanine (Phe), tryptophan (Trp), isoleucine (Ile), tyrosine (Tyr), methionine (Met), leucine (Leu), valine (Val), and the like.

In the α-helix polypeptide, the carboxyl group, which does not form a peptide bond and which is in the amino acid which forms the α-helix, can be made to be hydrophobic by esterification. On the other hand, an esterified carboxyl group can be made to be hydrophilic by hydrolysis.

The amino acid may be any of a L-amino acid, a D-amino acid, a derivative in which the side chain portion of a L-amino acid or a D-amino acid is modified, and the like.

The number of bonds (the degree of polymerization) of the amino acid in the α-helix polypeptide is not particularly limited and may be appropriately selected in accordance with the object. However, 10 to 5000 is preferable.

If the number of bonds (the degree of polymerization) is less than 10, it may not be possible for the polyamino acid to form a stable α-helix. If the number of bonds (the degree of polymerization) exceeds 5000, vertical orientation may be difficult to achieve.

Suitable specific examples of the α-helix polypeptide are polyglutamic acid derivatives such as poly(γ-methyl L-glutamate), poly(γ-ethyl L-glutamate), poly(γ-benzyl L-glutamate), poly(n-hexyl L-glutamate), and the like; polyaspartic add derivatives such as poly(β-benzyl L-aspartate) and the like; polypeptides such as poly(L-leucine), poly(L-alanine), poly(L-methionine), poly(L-phenylalanine), poly(L-lysine)-poly(γ-methyl L-glutamate), and the like.

The α-helix polypeptide may be a commercially available α-helix polypeptide, or may be appropriately synthesized or prepared in accordance with methods disclosed in known publications and the like.

As one example of synthesizing the α-helix polypeptide, the synthesis of block copolypeptide [poly(L-lysine)$_{25}$-poly(γ-methyl L-glutamate)$_{60}$]PLLZ$_{25}$-PMLG$_{60}$ is as follows. As is shown by the following formula, block copolypeptide [poly(L-lysine)$_{25}$-poly(γ-methyl L-glutamate)$_{60}$]PLLZ$_{25}$-PMLG$_{60}$ can be synthesized by polymerizing N$^\epsilon$-carbobenzoxy L-lysine N$^\alpha$-carboxy acid anhydride (LLZ-NCA) by using n-hexylamine as an initiator, and then polymerizing γ-methyl L-glutamate N-carboxy acid anhydride (MLG-NCA).

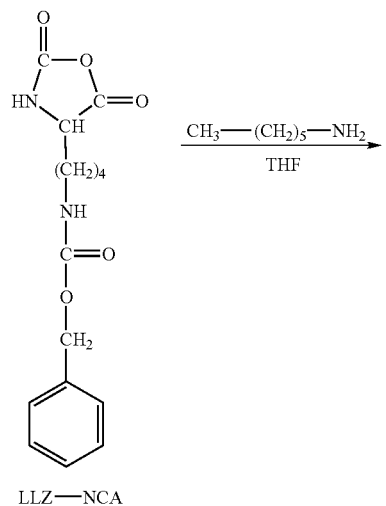

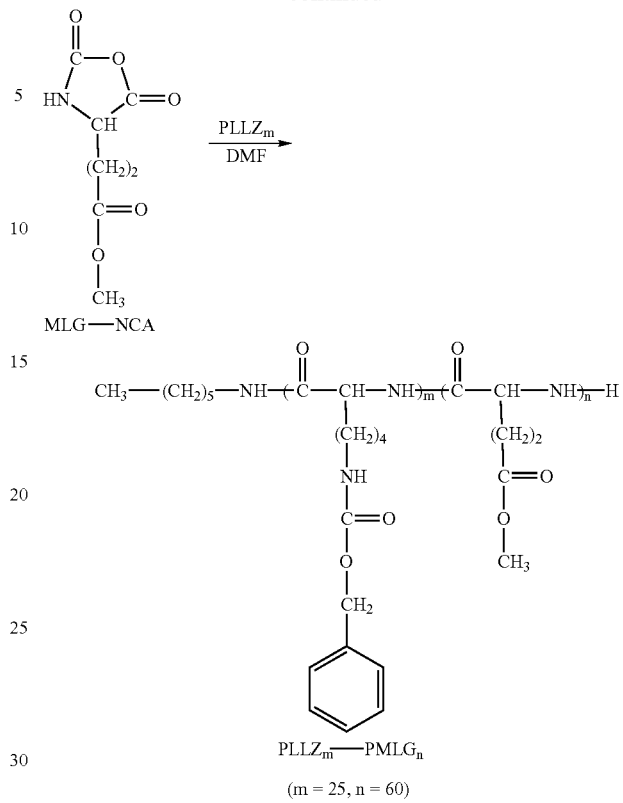

Synthesis of the α-helix polypeptide is not limited to the above-described method, and the α-helix polypeptide can be synthesized by a genetic engineering method. Specifically, the α-helix polypeptide can be manufactured by transforming a host cell by a expression vector in which is integrated a DNA which encodes the target polypeptide, and culturing the transformant, and the like.

Examples of the expression vector include a plasmid vector, a phage vector, a plasmid and phage chimeric vector, and the like.

Examples of the host cell include prokaryotic microorganisms such as *E. coli, Bacillus subtilis,* and the like; eukaryotic microorganisms such as yeast and the like; zooblasts, and the like.

The α-helix polypeptide may be prepared by removing the α-helix structural portion from a natural fibrous protein such as α-keratin, myosin, epidermin, fibrinogen, tropomyosin, silk fibroin, and the like.

{DNA}

The DNA may be a single-stranded DNA. However, the DNA is preferably a double-stranded DNA from the standpoints that the rod-shape can be stably maintained, other substances can be intercalated into the interior, and the like.

A double-stranded DNA has a double helix structure in which two polynucleotide chains, which are in the form of right-wound spirals, are formed so as to be positioned around a single central axis in a state in which they extend in respectively opposite directions.

The polynucleotide chains are formed by four types of nucleic acid bases which are adenine (A), thiamine (T), guanine (G), and cytosine (C). The nucleic acid bases in the polynucleotide chain exist in the form of projecting inwardly within a plane which is orthogonal to the central axis, and form so-called Watson-Crick base pairs. Thiamine specifically hydrogen bonds with adenine, and cytosine specifically hydrogen bonds with guanine. As a result, in a double-stranded DNA, the two polypeptide chains are bonded complementarily.

The DNA can be prepared by known method such as PCR (Polymerase Chain Reaction), LCR (Ligase Chain Reaction), 3SR (Self-Sustained Sequence Replication), SDA (Strand Displacement Amplification), and the like. Among these, the PCR method is suitable.

Further, the DNA can be prepared by being directly removed enzymatically from a natural gene by a restriction enzyme. Or, the DNA can be prepared by a genetic cloning method, or by a chemical synthesis method.

In the case of a genetic cloning method, a large amount of the DNA can be prepared by, for example, integrating a structure, in which a normal nucleic acid has been amplified, into a vector which is selected from plasmid vectors, phage vectors, plasmid and phage chimeric vectors, and the like, and then introducing the vector into an arbitrary host in which propagation is possible and which is selected from prokaryotic microorganisms such as *E. coli, Bacillus subtilis,* and the like; eukaryotic microorganisms such as yeast and the like; zooblasts, and the like.

Examples of chemical synthesis methods include liquid phase methods or solid phase synthesis methods using an insoluble carrier, such as a triester method, a phosphorous acid method, and the like. In the case of a chemical synthesis method, the double-stranded DNA can be prepared by using a known automatic synthesizing device and the like to prepare a large amount of single-stranded DNA, and thereafter, carrying out annealing.

{Amylose}

Amylose is a polysaccharide having a spiral structure in which D-glucose, which forms starch which is a homopolysaccharide of higher plants for storage, is joined in a straight chain by α-1,4 bonds.

The molecular weight of the amylose is preferably around several thousand to 150,000 in number average molecular weight.

The amylose may be a commercially available amylose, or may be appropriately prepared in accordance with known methods.

Amylopectin may be contained in a portion of the amylose.

The length of the rod-shaped body is not particularly limited, and may be appropriately selected in accordance with the object. However, from the standpoint of causing light reflection of the incident light as colored interference light which will be described later, a length of 810 nm or less is preferable, and 10 nm to 810 nm is more preferable.

The diameter of the rod-shaped body is not particularly limited, and is about 0.8 to 2.0 nm in the case of the α-helix polypeptide.

The entire rod-shaped body may be hydrophobic or hydrophilic. Or, the rod-shaped body may be amphiphilic such that a portion thereof is hydrophobic or hydrophilic, and the other portion thereof exhibits the opposite property of the one portion. In the case of an amphiphilic rod-shaped body, the numbers of the lipophilic (hydrophobic) portions and hydrophilic portions are not particularly limited, and may be appropriately selected in accordance with the object. Further, in this case, the portions which are lipophilic (hydrophobic) and the portions which are hydrophilic may be positioned alternately, or either type of portion may be positioned only at one end portion of the rod-shaped body.

In the case of the amphiphilic rod-shaped body, there is no particular limitation for the numbers of the moiety showing hydrophobicity and the moiety showing hydrophilicity but that may be appropriately selected according to the object. In that case, the moiety showing hydrophobicity and the moiety showing hydrophilicity may be alternately positioned. Any of the moieties may be positioned only at one end of the rod-shaped body.

<Target Nucleic Acid>

For the target nucleic acid, there is no particular limitation but may be appropriately selected depending on the object although it is preferred to be a nucleic acid selected from a part of a base sequence which is present in prokaryotes only, a part of a base sequence which is present in eukaryotes (except human being) only and a part of a base sequence which is present in human being only. It is not necessary that the target nucleic acid is a nucleic acid which is a final target in the detection for each of the objects but may be a nucleic acid which co-exists with the nucleic acid of the final target for detection.

For the target nucleic acid, there may be specifically exemplified cancer-related gene, gene related to genetic diseases, virogene, bacterial gene, gene showing polymorphism called a risk factor for diseases, and the like.

For the cancer-related gene, examples include K-ras gene, N-ras gene, p53 gene, BRCA1 gene, BRCA2 gene, src gene, ros gene, APC gene, and the like.

For the gene related to genetic diseases, examples include genes of various inborn error metabolisms such as phenylketonuria, alkaptonuria, cystinuria, Huntington's chorea, Down syndrome, Duehénne muscular dystrophy, hemophilia, and the like.

For the virogene and bacterial gene, examples include genes of hepatitis C virus, hepatitis B virus, influenza virus, measles virus, HIV virus, mycoplasma, rickettsia, streptococcus, salmonella, and the like.

The gene showing polymorphism means a gene which has a base sequence being not always directly related to the cause of the disease, and the like. and being different for each body. Examples include PS1 (presenilin 1) gene, PS 2 (presenilin 2) gene, APP (β-amyloid precursor protein) gene, lipoprotein gene, gene related to HLA (human leukocyte w antigen) and blood type, gene believed to be related to onset of hypertension, diabetes and the like, and the like.

Usually, those genes are present on chromosomes of the host but, in some cases, they are coded by mitochondria gene.

For the sample to be examined containing the target antigen as such, examples include pathogenic organism such as bacteria and virus; blood, saliva, disease tissue pieces, and the like. separated from living organism; and excrement such as feces and urine. Further, when diagnosis before birth is carried out, cells of fetus existing in amniotic fluid and a part of divided ovules may be also used as a sample to be examined. Furthermore, such a sample to be examined may be used either directly or, if necessary, after concentrating as a precipitate by a centrifugal operation or the like and then subjected to a cytocidal treatment such as, for example, enzymatic treatment, thermal treatment, surfactant treatment, ultrasonic treatment or a combination thereof. In that case, the cytocidal treatment is carried out with an object of manifesting the DNA derived from the aimed tissue.

Incidentally, protein which is essential for cell division and has been known to specifically bond to DNA such as tubulin, chitin, and the like which is not nucleic acid is also included in the target substance of the present invention.

<Nucleic Acid Specifically Bonding to Target Nucleic Acid>

The nucleic acid which specifically bonds to the nucleic acid is RNA or a single-stranded DNA having a base sequence complementary to the target nucleic acid. Such a nucleic acid is able to be prepared by PCR method, chemical synthetic method, and the like as same as above.

There is no limitation for the length of nucleic acid as long as it is able to hybridize to a target nucleic acid in a stable manner under a usual hybridizing condition. Still it is preferred not to be unnecessarily long and is preferably to be 10–50 bases, more preferably 10–30 bases and, still more preferably, 15–25 bases.

When the resulting nucleic acid which specifically bonds to a target nucleic acid is bonded to the rod-shaped body, a hybridization probe of the present invention is prepared.

The bonding method may be appropriately selected depending on the nucleic acid the rod-shaped body and there may be used known methods such as a method in which covalent bond such as ester bond, amide bond, and the like. is utilized; a method in which protein is labeled with avidin and bonded to biotinated nucleic acid; a method in which protein is labeled with streptoavidin and bonded to biotinated nucleic acid; and the like.

For the covalent bond method, examples include peptide method, diazo method, alkylation method, cyan bromide activation method, bonding method by a cross-linking reagent, inmobilization method utilizing Ugi reaction, immobilization method utilizing a thiol-disulfide exchange reaction, Schiff base formation method, chelate bonding method, tosyl chloride method, biochemically specific bonding method, and the like. For more stable bonding such as covalent bond, there is preferably carried out utilizing a reaction of thiol group with maleimide group, a reaction of pyridyl disulfide group with thiol group, a reaction of pyridyl disulfide group with thiol group, a reaction of amino group with aldehyde group, and the like and there may be applied a method which is appropriately selected from known methods, methods which may be easily carried out by the persons skilled in the art and methods which are modified therefrom. Among them, there may be used a chemically bonding agent and a cross-linking agent which are able to form more stable bond.

For such chemically bonding agent and cross-linking agent, examples include carbodiimide, isocyanate, diazo compound, benzoquinone, aldehyde, periodic acid, maleimide compound, pyridyl disulfide compound, and the like. For the preferred reagent, examples include glutaraldehyde, hexamethylene diisocyanate, hexamethylene diisothiocyanate, N,N'-polymethylenebisiodoacetamide, N,N'-ethylenebismaleiimide, ethylene glycol bissuccinimidyl succinate, bisdiazobenzidine, 1-ethyl-3-(3-dimethylaminopropyl) carbodiimide, succinimidyl 3-(2-pyridylthio) propionate (SPDP), N-succinimidyl 4-(N-maleimidomethyl) cyclohexane-1-carboxylate (SMCC), N-sulfosuccinimidyl 4-(N-maleimidomethyl) cyclohexane-1-carboxylate, N-succinimidyl (4-iodoacetyl) aminobenzoate, N-succinimidyl 4-(1-maleimidophenyl) butyrate, iminothiolane, S-acetylmercaptosuccinic acid anhydride, methyl-3-(4'-dithiopyridyl) propionimidate, methyl-4-mercaptobutyryl imidate, methyl-3-mercaptopropionimidate, N-succinimidyl-S-acetyl mercaptoacetate, and the like.

<Hybridization Probe>

As shown in FIG. 1, the hybridization probe 10 of the present invention has a rod-shaped body 1 and nucleic acid 2 which is bonded to the rod-shaped body 1 and specifically bonds to a target nucleic acid. In the hybridization probe 10, when the target nucleic acid is bonded to the nucleic acid moiety, properties of the hybridization probe such as refractive index and transmittance of light, mass, viscoelasticity, and the like change and, therefore, when the change is detected, it may be utilized for the detection of the target nucleic acid.

The above method for the detection may be appropriately selected depending on the object and, for example, various methods such as that color change is observed by naked eye, that wavelength change is detected by spectrophotometer, that oscillation of frequency of quartz oscillator, surface acoustic wave (SAW) element or the like is detected by a frequency counter, and the like may be carried out.

This hybridization probe 10 may be used as it is and, in that case, when it is used by aligned in single or plural layer(s) on the surface of a solvent containing the target nucleic acid or at the boundary between the solvent and an immisible liquid, changes in wavelength may be easily detected and, therefore, that is preferred.

It is also able to be formed in a film-like state such as monomolecular film or two layered monomolecular films on a substrate which is vertically aligned by, for example, a Langmuir-Brodgett (HYBRIDIZATION PROBE) technique and the above is preferred in such respects that changes in wavelength may be apt to be detected, that quartz oscillator, surface acoustic wave (SAW) element or the like may be fixed, that handling is easy, and the like.

For the hybridization probe of the present invention, the one in which to reflect an incident light as colored interference light is preferred from a viewpoint of recognition and discrimination.

The reflection of the incident light as colored interference light is a color formation resulted on the basis of a multi-layer thin film interference theory which is a basic principle of color formation of the scaly powder of the wings of a Morpho butterfly and is a color formation on the film as a result of reflection of light of specific wavelength corresponding to the thickness of the film and the refractivity thereof when stimulation from outside such as electric field, magnetic field, heat, light (for example, natural light, infrared light and ultraviolet light), and the like is applied to the film. The color tone may be freely controlled like the surface skin of chameleon by the stimulation from outside.

Principle of the light reflection of the incident light as colored interference light will be described herein after.

Figure 2:
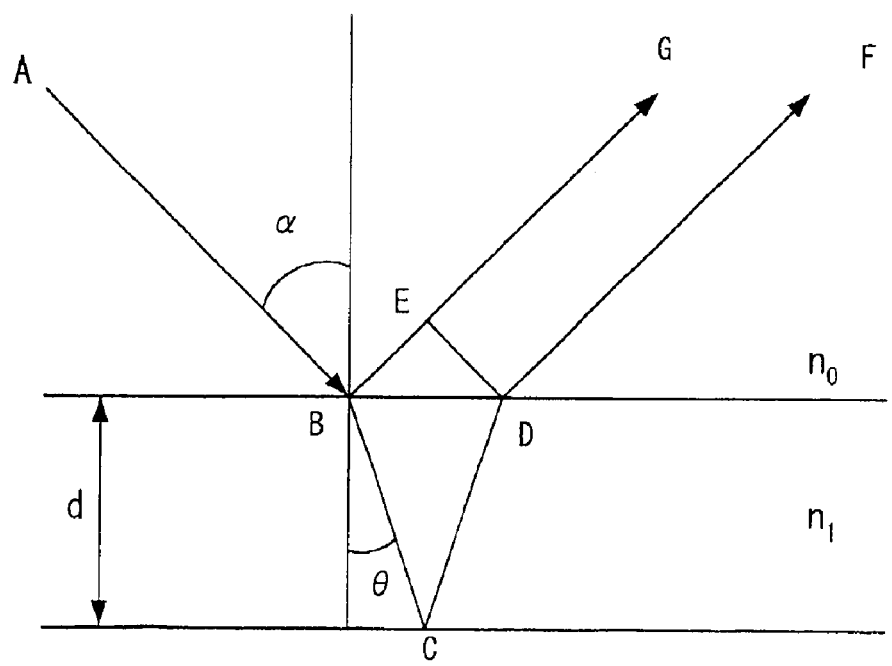
FIG. 2 is a view for explaining a principle of light reflection of the incident light as colored interference light.
Figure 3:
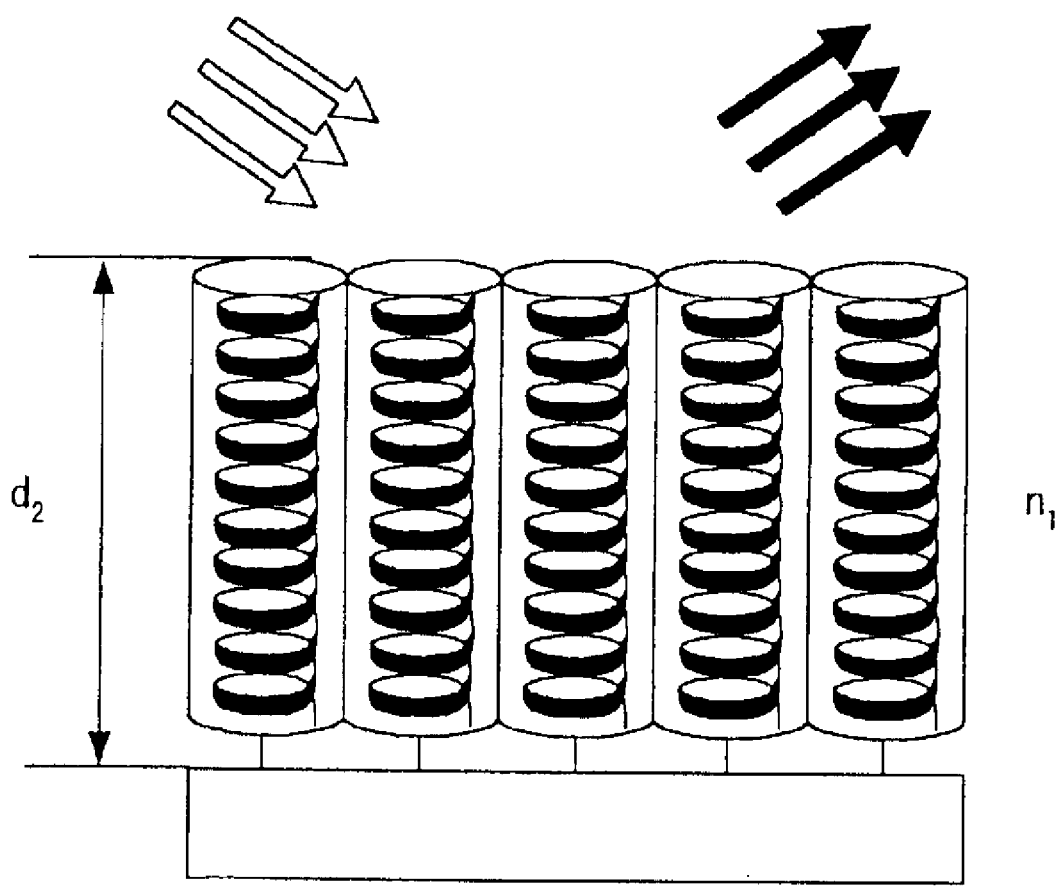
FIG. 3 is a typical view to explain the principle of light reflection of the incident light as colored interference light.

As shown in FIG. 2 and FIG. 3, when light is irradiated on the film of the rod-shaped body, wavelength (λ) of the interference light by the film is emphasized under the condition as shown in the following (1) and enfeebled under the condition as shown in the following (2).

$$\lambda = \frac{2tl}{m}\sqrt{n^2 - \sin^2\alpha} \quad (1)$$

$$\lambda = \frac{4tl}{2m-1}\sqrt{n^2 - \sin^2\alpha} \quad (2)$$

In the formulae (1) and (2), the λ means wavelength (nm) of the interference light, the α means angle of incidence (degree) of the light to the film, the t means thickness (nm) of a single film, the 1 means numbers of the film, the n means a refractive index of the film and the m means an integer of 1 or more.

The light reflection of the incident light as colored interference light may be achieved by aligning the hybridization probe in a film-like shape.

Thickness of the single film is preferably 810 nm or less and, more preferably, it is from 10 nm to 810 nm.

When the thickness is changed suitably, a color (wavelength) of the light interfered by the light reflection of the incident light may be changed.

The film may be either a monomolecular film or a layered film comprising the monomolecular film.

The monomolecular film or the layered film comprising the same may be formed by, for example, a Langmuir-Brodgett method (LB method) and, in that case, a known LB film forming apparatus (such as NL-LB 400 NK-MWC manufactured by Nippon Laser & Electronics Laboratories) may be used.

Figure 4:
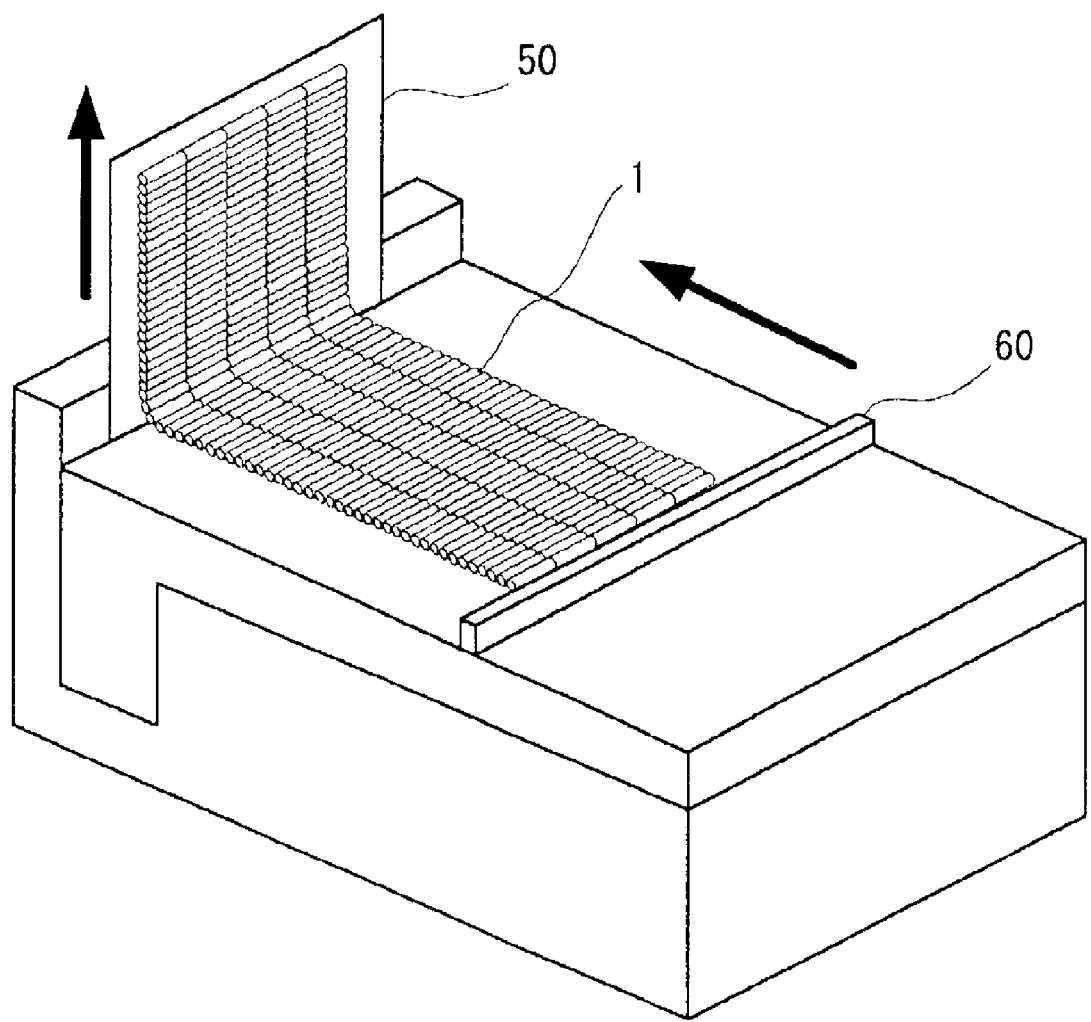
FIG. 4 is a schematic view for showing a formation of a monomolecular film by a functional molecule of the present invention.

Formation of the monomolecular film may be carried out, for example, in such a state that the above mentioned rod-shaped body which is lipophilic (hydrophobic) or amphiphilic is floated on water surface (on an aqueous phase) or in such a state that the rod-shaped body which is lipophilic (hydrophobic) or amphiphilic is floated on oil surface (on an oil phase) or, in other words, the rod-shaped body 1 is aligned as shown in FIG. 4 so as to form on a substrate 50 using an extrusion material 60. When such an operation is repeatedly carried out, the layered film where the monomolecular films are layered in any number may be formed on the substrate 50. Incidentally, it is preferred that the monomolecular film or the layered film is fixed on the substrate 50 since the reflection of the incident light as colored interference light by the monomolecular film or layered film is expressed in a stable manner.

In that case, there is no particular limitation for the substrate 50 and, according to the object, its material, shape, size, and the like may be appropriately selected although it is preferred that its surface is appropriately subjected to a surface treatment previously with an object that the rod-shaped body 1 is easily aligned thereto. When the rod-shaped body 1 (such as α-helix polypeptide) is hydrophilic for example, it is preferred that a surface treatment such as hydrophilizing treatment using octadecyl trimethylsiloxane and the like is previously carried out.

Figure 5:
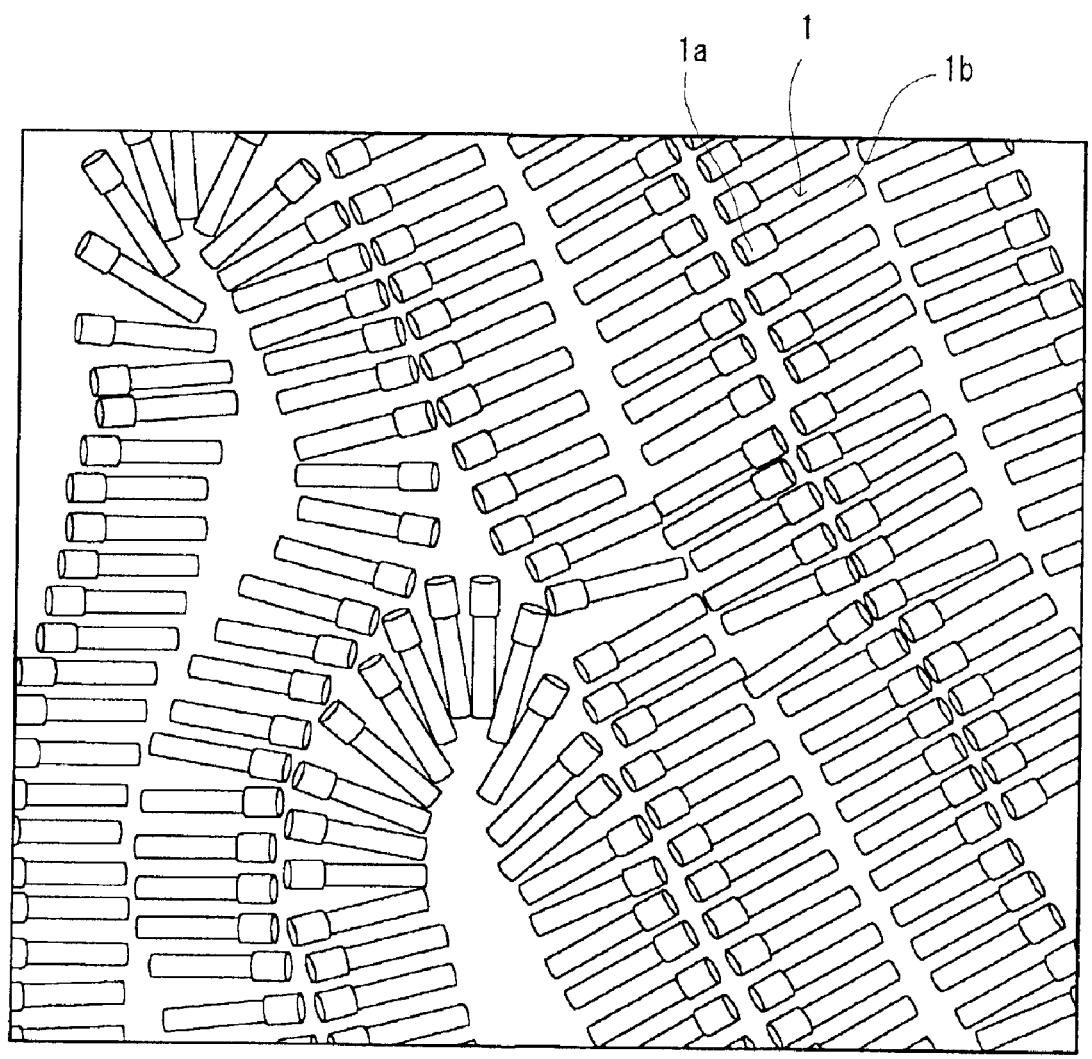
FIG. 5 is a schematic view for showing an example of an amphiphilic functional molecule aligned on water (aqueous phase).

With regard to the state where the rod-shaped body is floated on an oil phase or an aqueous phase in the formation of the monomolecular film of the amphiphilic rod-shaped body, the lipophilic areas (hydrophobic areas) 1a of the rod-shaped body 1 are aligned in an adjacent state each other on the aqueous phase or oil phase while the hydrophilic areas 1b are aligned in an adjacent state each other as shown in FIG. 5.

Figure 6:
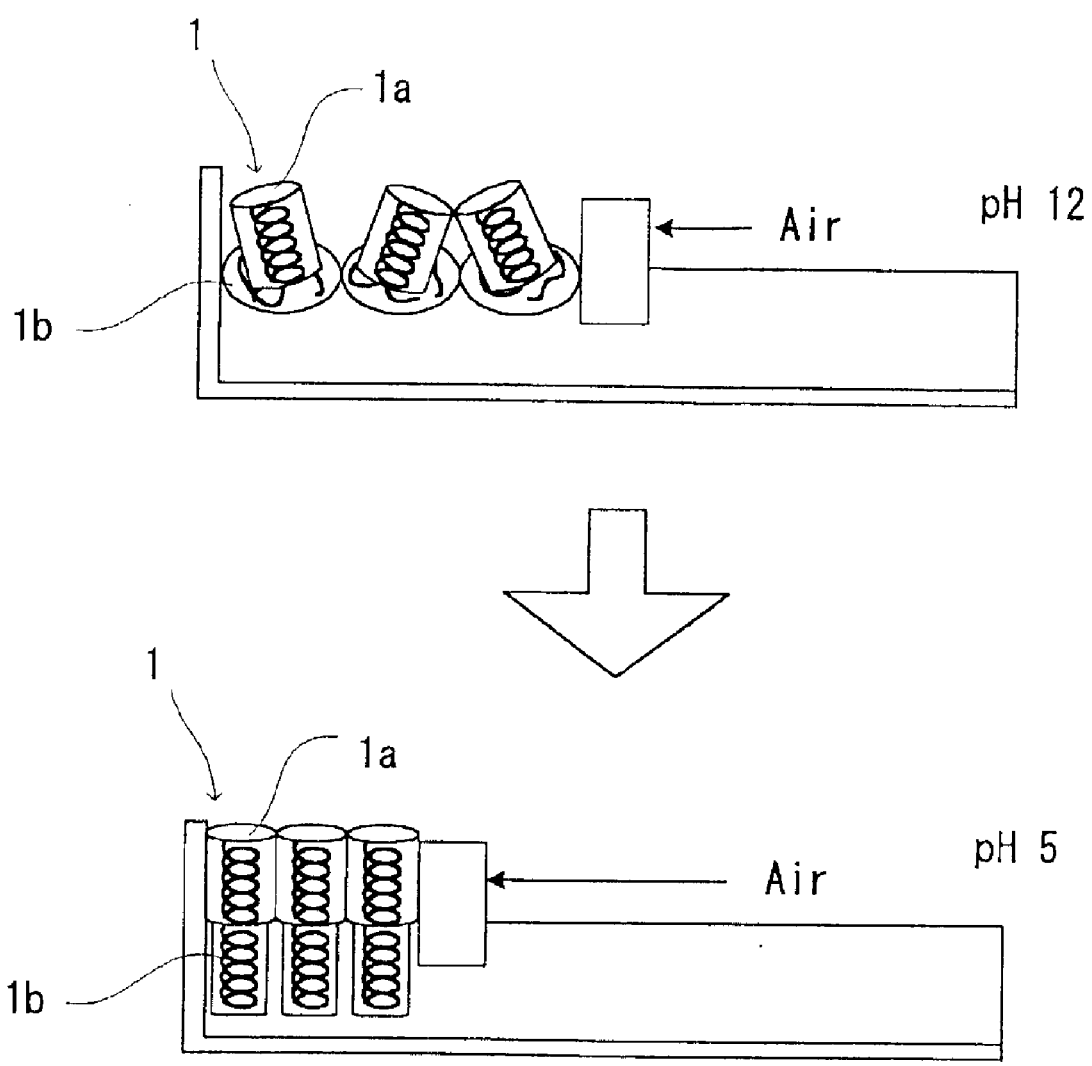
FIG. 6 is a schematic view for showing an example of an amphiphilic functional molecule vertically aligned on water (aqueous phase).

The above is an example of a layered membrane or a layered film comprising the same where the rod-shaped body is aligned in the plane direction of the monomolecular film (in a horizontal state) while a monomolecular film where the rod-shaped body is aligned in the thickness direction of the monomolecular film (in a vertical state) may be manufactured, for example, as follows. First, as shown in FIG. 6, water (aqueous phase) is made alkaline of around pH 12 under such a state that the amphiphilic rod-shaped body 1 (α-helix polypeptide) is floated on the water surface (aqueous phase) (i.e., in a horizontal state). As a result, in the hydrophilic area 1b in the rod-shaped body 1 (α-helix polypeptide), the α-helix structure thereof is disentangled to give a random structure. At that time, the lipophilic area (hydrophobic area) 1a of the rod-shaped body 1 (α-helix polypeptide) maintains its α-helix structure. Then, pH of the water (aqueous phase) is made acidic to about 5 thereby the hydrophilic area 1b in the rod-shaped body 1 (α-helix polypeptide) forms an α-helix structure again. When the pushing material attached to the rod-shaped body 1 (α-helix polypeptide) is pushed by the pressure of air from its side to the rod-shaped body 1 (α-helix polypeptide), the rod-shaped body 1 maintains vertical against water (aqueous phase) while its hydrophilic area 1b forms an α-helix structure in the direction substantially orthogonal to the water surface in the aqueous phase. When the aligned rod-shaped body 1 (α-helix polypeptide) is pushed out onto the substrate 50 using a pushing material 60 as mentioned above by referring to FIG. 4, it is possible to form a monomolecular film on the substrate 50. When such operation is repeatedly carried out, the layered film having prescribed number of monomolecular film may be formed on the substrate 50.

With regard to the hybridization probe which is able to give single-layered film or multi-layered film which reflects incident light as colored interference light, there may be exemplified an hybridization probe which is amphiphilic and an amphiphilic hybridization probe wherein the rod-shaped body is α-helix polypeptide is preferred.

In the hybridization using the hybridization probe of the present invention, there have been commonly used SSC (20×SSC: 3M sodium chloride, 0.3M sodium citrate), SSPE (20×SSPE: 3.6M sodium chloride, 0.2M sodium phosphate, 2 mM EDTA), and the like and, in the present invention, those solutions may also be used by diluting to an appropriate concentration. If necessary, it is preferred to carry out in a hybridization solution containing an organic solvent such as dimethyl sulfoxide (DMSO), dimethyl formamide (DMF), and the like, formamide, salt, protein, stabilizer, buffer, and the like.

Concentration of the formamide is 0–60% by mass, preferably 10–50% by mass and, more preferably, 20–30% by mass. For the salt, examples include inorganic salts such as sodium chloride, potassium chloride, and the like and organic salts such as sodium citrate, sodium oxalate, and the like and the salt concentration is 0–2.0 M or, preferably, 0.15–1.0 M. For the protein, examples include serum albumin, and the like. For the stabilizer, examples include phycol, and the like. For the buffer, examples include a phosphate buffer, and the like and its preferred concentration is 1–100 mM.

The hybridization using the hybridization probe may be carried out in such a manner that the hybridization probe and a sample nucleic acid (single-stranded DNA or single-stranded RNA) are added to the hybridization solution to an extent of equimolar concentration, heated at 60–90° C. for 1–60 minute(s) and then gradually cooled down to 0–40° C. during 1–24 hour(s).

<Target Nucleic Acid Detecting kit>

The target nucleic acid detecting kit of the present invention contains a hybridization probe having a rod-shaped body with a length of 810 nm or shorter and nucleic acid which is bonded to the rod-shaped body and specifically bonds to a target nucleic acid and causing a light reflection of the incident light as colored interference light when aligned in a film-like shape; and any of dish, plate and tube.

The target nucleic acid detecting kit may contain a solvent containing the hybridization probe in an amount suitable for the size of the dish, and the like in a container which is different from the container. For example, an aqueous sample is added to the container and the oily or amphiphilic hybridization probe is added to the sample so that the hybridization probe is aligned on the sample in a film-like shape in which a target nucleic acid may be detected by the changes in wavelength based on the light reflection of an incident light as colored interference light of the film-like probe.

If necessary, the detecting kit may be combined with cytocidal reagent for a pretreatment of the sample, washing liquid for washing the amplified reaction product, oil for preventing the evaporation of water from the reaction solution, and the like.

In the target nucleic acid detecting kit of the present invention, the hybridization probe aligned in a film-like shape reflects the incident light as colored interference light on the basis of the multi-layered thin film interference theory which is a basic principle for color formation of the scaly powder of the wings of a Morpho butterfly. Accordingly, When the change in wavelength based on the reflection of the incident light as colored interference light brought out by changes in length or refractive index at the time the film-like hybridization probe hybridizes with a target nucleic acid is measured, it is now possible to detect the target nucleic acid in the sample by a simple operation in a reliable manner.

<Target Nucleic Acid Detecting Apparatus>

The target nucleic acid detecting apparatus according to the first embodiment of the present invention is equipped with a hybridization probe having a rod-shaped body of a length of 810 nm or shorter, nucleic acid which is bonded to the rod-shaped body and bonds to a target nucleic acid and reflecting the incident light as colored interference light when aligned in a film-like shape; a sample adding means in which the hybridization probe is contacted to a sample; and a colored wavelength measuring means in which changes in wavelength based on the reflection of the incident light as colored interference light brought out by changes in length or refractive index at the time the film-like hybridization probe hybridizes with a target nucleic acid is measured.

For the sample, there is no particular limitation as long as it is a thing which is an object of the test whether or not it contains the target nucleic acid and examples include the sample to be tested, a nucleic acid library containing a target nucleic acid, and the like.

For an appropriate embodiment of the target nucleic acid detecting apparatus, it is preferred that the hybridization probe is further amphiphilic and that the sample adding means is a sample adding means in which the hybridization probe is added to an aqueous sample together with an oil phase so that the hybridization probe is contacted to the sample.

For the sample adding means, there is no particular limitation as long as it is a means for adding a predetermined amount of hybridization probe to the sample or is a means for adding a predetermined amount of sample to the hybridization probe. It is however preferred that the amount of the hybridization probe is set in such an amount that the light reflection of an incident light as colored interference light may apt to be detected by aligning in a film-like shape.

The fact that the hybridization probe is amphiphilic is preferred because of such a view that the probe is vertically aligned at the interface between an oil phase and an aqueous phase in which changes in wavelength due to the light reflection of an incident light as colored interference light are easily measured.

In accordance with the target nucleic acid detecting apparatus according to the first embodiment, when the nucleic acid having a base sequence complementary to the target nucleic acid of the hybridization probe is hybridized to the target nucleic acid, length or refractive index of the probe aligned in a film-like shape changes and, when the change in wavelength based on a colored interference light brought about by the incident light reflection of the probe is measured by a colored wavelength measuring means such as a spectrophotometer, it is now possible to specifically test whether the target nucleic acid is present. In addition, when a calibration curve is previously prepared using a sample DNA in a known amount, concentration of DNA in the sample to be detected or quantified may be detected or quantified.

The target nucleic acid detecting apparatus according to the second embodiment of the present invention comprises a biosensor the hybridization probe of the present invention is aligned on quartz oscillator or surface acoustic wave (SAW) element in a film-like shape, an oscillation circuit whereby changes in mass or changes in viscoelasticity when a target nucleic acid is hybridized to the biosensor are oscillated as frequency and a frequency counter whereby frequency of the oscillation oscillated from the oscillation circuit is measured.

In that case, it is preferred that the hybridization probe is aligned in a monomolecular film-like shape to the quartz oscillator or surface acoustic wave (SAW) element or is aligned in a bimolecular film-like shape thereto. For the frequency counter, there is no particular limitation as long as it can precisely measure the frequency from the quartz oscillator or the surface acoustic wave (SAW) element.

Figure 7A:
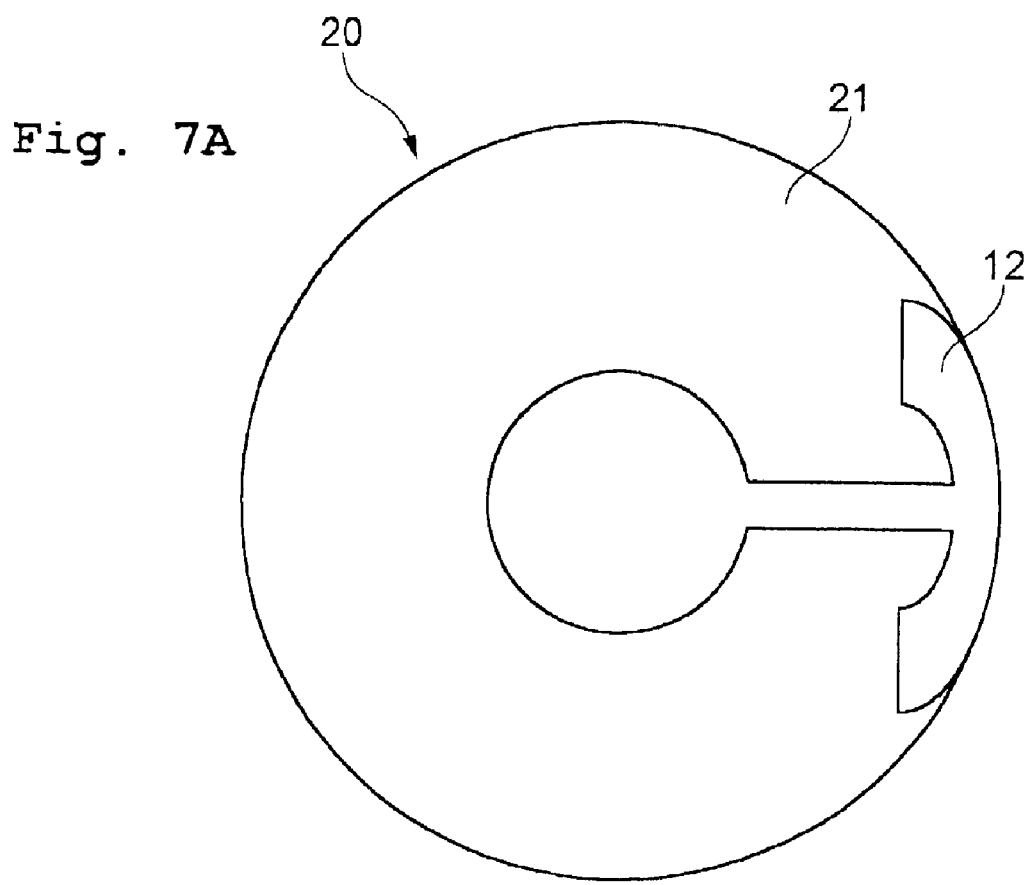
Figure 7B:
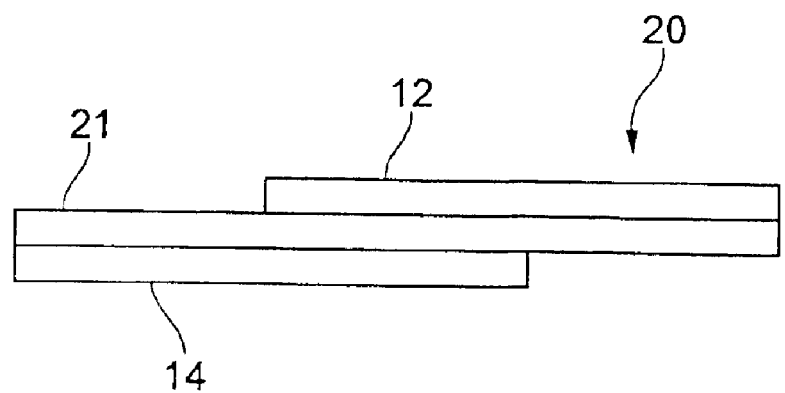

In the quartz oscillator, metal electrodes are vapor deposited on the surface and the back of a thin quartz plate. An example of the quartz oscillator 20 is shown in FIG. 7A and 7B. FIG. 7A is a plane view while FIG. 7B is a front view. An electrode 12 is vapor deposited on the surface of the quartz plate 21 while another electrode 14 is vapor deposited on the back thereof. The electrodes extend to the left side from the electrodes 12, 14 and the left ends thereof are connected to clip-type lead wires (not shown) followed by connecting to an alternating current source (not shown). When alternating current is applied between the electrodes 12, 14, there is generated oscillation of a predetermined period in the quartz plate 21 due to a back piezoelectric effect.

Although not shown in the drawing, an hybridization probe film is aligned on the surface of the quartz oscillator 20. The antibody of this hybridization probe film is bonded to the target antigen and mass of the surface of the quartz oscillator 20 changes to an extent of the mass of the bonded target antigen whereby a resonance frequency changes.

Between the changes in the resonance frequency and changes in the mass of the hybridization probe film coated on the surface of the quartz oscillator 20 which oscillates in parallel to the plane vertical to the thickness direction, there is a relation as shown in the following formula (3) whereby changes in the mass may be detected from changes in the resonance frequency. For example, in the case of an oscillator of resonance frequency of 9 MHz (area: about 0.5 cm$^2$), a reduction in frequency of 400 Hz is resulted by an increase in mass of 1 μg.

$$\Delta F = -2.3 \times 10^6 (F^2 \times \Delta W/A) \tag{3}$$

In the formula, F means resonance frequency (MHz) of the quartz oscillator, $\Delta F$ means changes (Hz) in the resonance frequency by changes in mass, $\Delta W$ means changes in mass (g) of the film and A means a surface area (cm$^2$) of the film.

Figure 8:
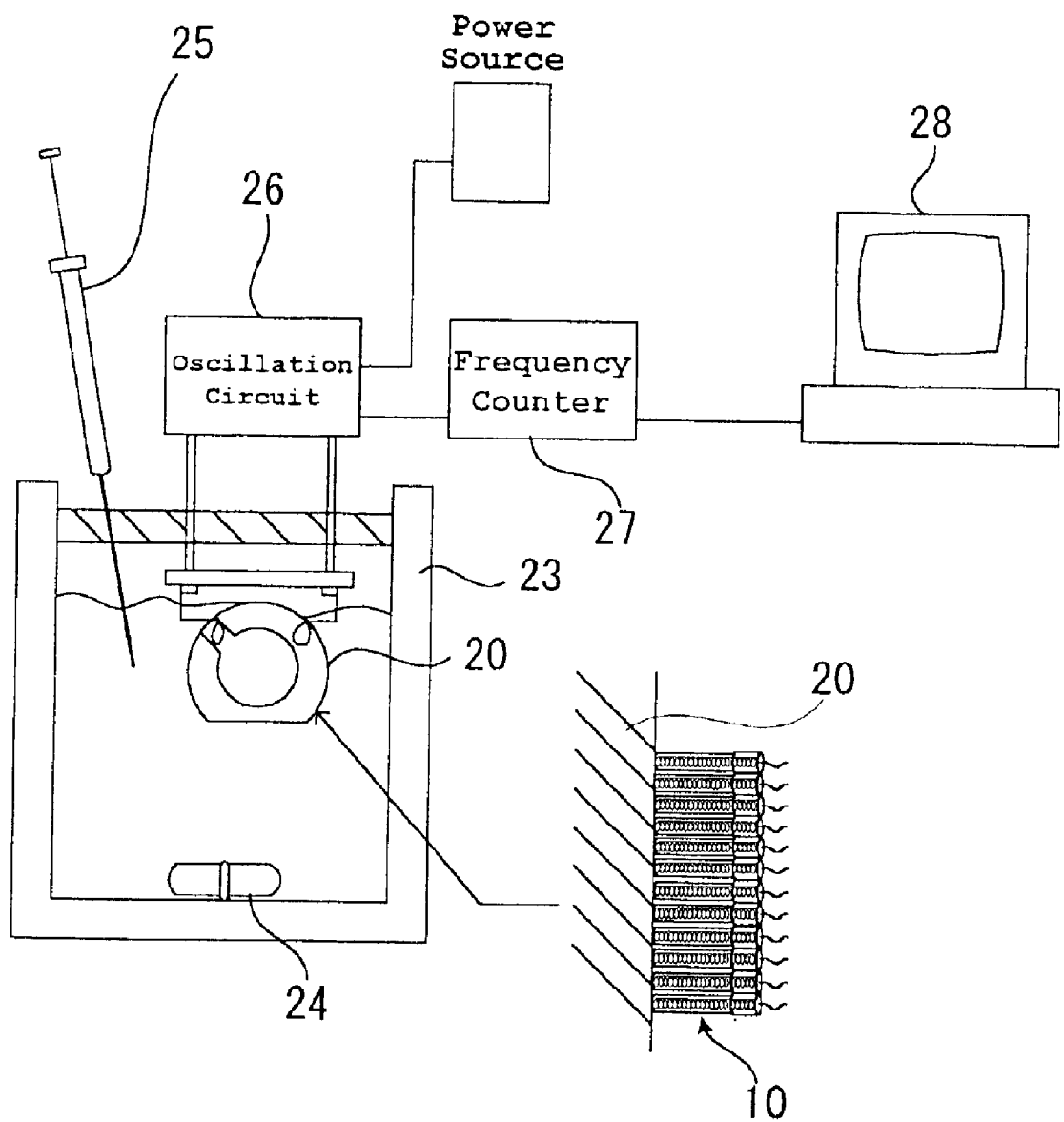
FIG. 8 is a schematic view which shows an example of a nucleic acid detecting apparatus.

An example of the nucleic acid detecting apparatus is shown in FIG. 8. The quartz oscillator 20 (hybridization probe 10 is aligned on the surface in a film-like shape) is attached to an arm for attaching the quartz oscillator and dipped in a solution in a thermostat heat block 23. The thermostat heat block 23 maintains the temperature of the solution constant. The solution is stirred by a stirrer 24. In a sample injection 25, a sample to be measured is injected into a solution. In the oscillation circuit 26, alternating current field is applied to the electrodes 12, 14 of the quartz oscillator 20 to oscillate the quartz oscillator 20. Oscillation frequency of the oscillation circuit 24 is counted by a counter 27, analyzed by a computer 28 and mass of the target antigen in the sample is indicated.

As such, when a nucleic acid having a base sequence complementary to the target nucleic acid of the hybridization probe is hybridized to the target nucleic acid, mass of the probe changes and the quartz oscillator catches the change in mass and converts to frequency. Accordingly, when the changes in frequency are measured by the frequency counter, it is now possible to specifically test whether the target nucleic acid is present.

When a calibration curve is previously prepared using a sample DNA in a known amount, it is also possible to detect or quantity the concentration of DNA in the sample to be detected or quantified.

The surface acoustic wave (SAW) element is an element where a pair of comb-shaped electrodes is set on the surface of the solid and electric signal is converted to a surface acoustic wave (sonic wave transmitting the solid surface, ultrasonic wave), transmitted to the encountering electrode and outputted as electric signal again whereby signal of specific frequency corresponding to the stimulation may be taken out. Ferroelectric substance such as lithium tantalite and lithium niobate, quartz, zinc oxide thin film, and the like are used as the material therefor.

The SAW is elastic wave which transmits along the surface of the medium and exponentially decreases in the inner area of the medium. In the SAW, the transmitted energy is concentrated on the surface of the medium whereby the changes in the medium surface may be sensitively detected and, as a result of the changes in the mass of the surface, the SAW transmitting velocity changes as same as in the case of quartz oscillator. Usually, SAW transmitting velocity is measured as the changes in oscillation frequency using an oscillation circuit. Changes in the oscillation frequency are given by the following formula.

$$\Delta f = (k_1 + k_2) f^2 h \rho - k_2 f^2 h [(4\mu/V_r^2)(\lambda + \mu/\lambda + 2\mu)]$$

In the formula, $k_1$ and $k_2$ mean constants, h means thickness of the fixed film, $\rho$ means density of the film, $\lambda$ and $\mu$ mean Lame constants of the film and $V_r$ means a SAW transmitting velocity.

Figure 9:
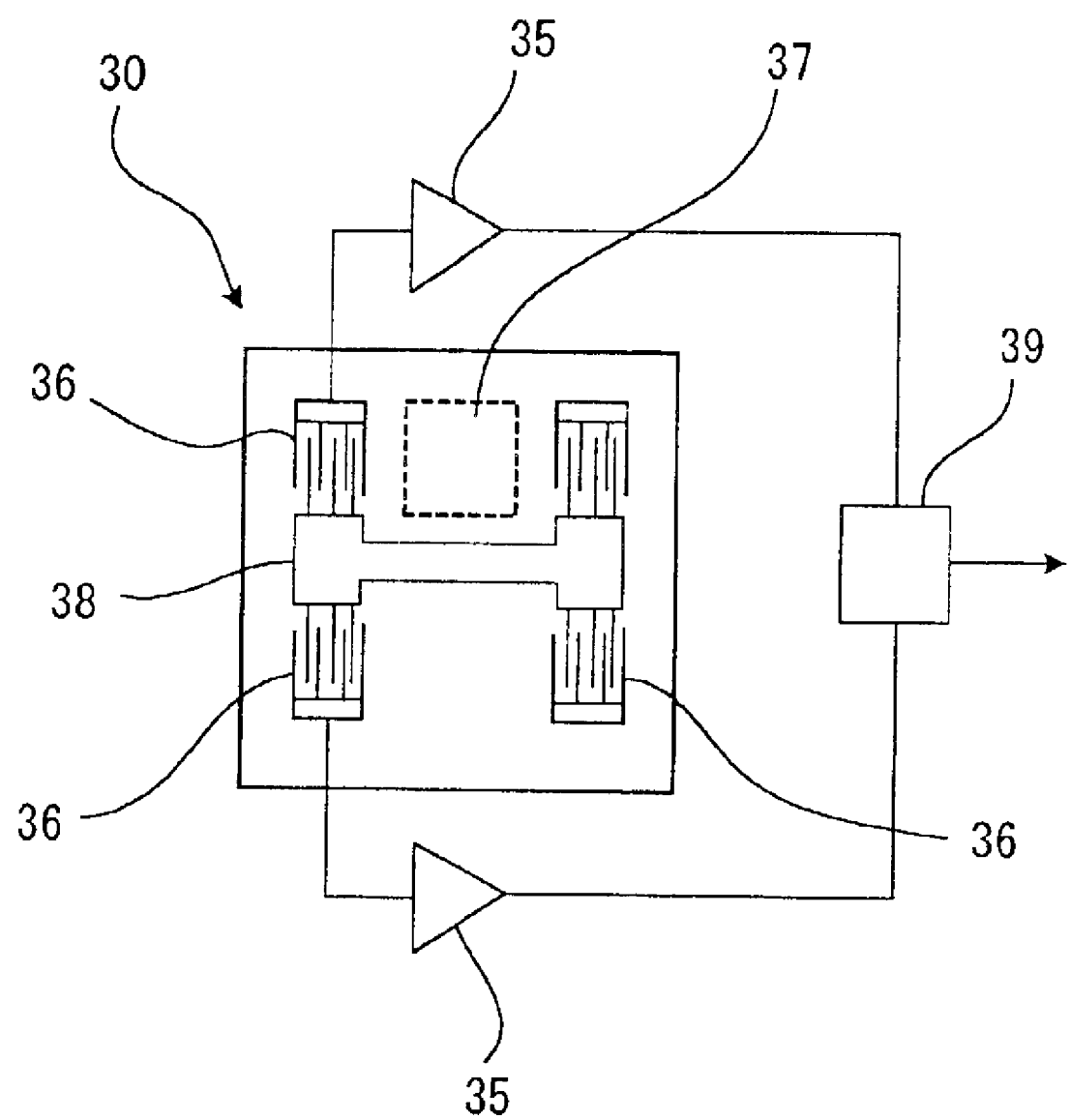
FIG. 9 is a schematic plan view showing a surface acoustic wave (SAW) element.

FIG. 9 is a schematic plane view which shows an example of constitution of main parts of a surface acoustic wave (SAW) element. In FIG. 9, in the SAW element sensor 30, there are formed gold electrode 38 and comb-shaped electrodes 36 at both ends thereof on the SAW element having a resonance frequency of 90 MHz made of an ST cut quartz and there is formed a film (not shown) comprising the hybridization probe in the surface wave transmitting region 37 as shown by dotted lines. The sensor is connected to a frequency counter 39 from each comb-shaped electrode 36 via a high-frequency amplifier 35 whereby the mass of the object to be captured in the sample is indicated.

When a nucleic acid having a base sequence complementary to the target nucleic acid of the hybridization probe is hybridized to the target nucleic acid, mass or viscoelasticity of the probe changes and the surface acoustic wave (SAW) catches the change in mass or viscoelasticity and converts to frequency. Accordingly, when the changes in the frequency are measured by the frequency counter, it is now possible to specifically test whether the target nucleic acid is present.

When a calibration curve is previously prepared using a sample antigen of a known amount, the antigen concentration to be detected or quantified in the sample may be detected or quantified.

For a method of chemical bonding/fixing of the hybridization probe on the electrode of the quartz oscillator or surface acoustic wave (SAW) element constituting the biosensor, there is no particular limitation but may be appropriately selected depending on the object. For example, that may be carried out by means of a chemical bond such as a covalent bond.

The above-mentioned covalent bond method is not particularly limited, however, the same method which is used for bonding of nucleic acid to rod-shaped body in the hybridization probe may be appropriately selected and used.

To be specific, examples include a method in which a substance in which thiol group is introduced into the end of the hybridization probe is synthesized, then quartz oscillator or surface acoustic wave (SAW) element is dipped into the above solution and is made to react therewith and, after that, the biosensor is taken out from the solution and dried. With regard to the thiol group, S-trimethyl-3-mercaptopropyloxy-β-cyanoethyl-N,N-diiso-propylaminophosphoramidide or the like is covered and introduction of the thiol group into the end of the probe may be carried out by a phosphoramide method.

<Target Nucleic Acid Detecting Method>

The target nucleic acid detecting method according to the present invention comprises a contacting step in which a hybridization probe having a rod-shaped body of a length of 810 nm or shorter, having nucleic acid which is bonded to the rod-shaped body and specifically bonds to a target nucleic acid, reflects the incident light as colored interference light when aligned in a film-like shape and being amphiphilic with a sample; and a wavelength measuring step in which changes in wavelength caused by the light reflection of the incident light as colored interference light of the film-like hybridization probe hybridized to the target nucleic acid.

For the contacting step, there is no particular limitation but may be carried out by the same condition and method as in the case of common hybridization.

For the colored wavelength measuring step, there is no particular limitation so long as it is a method in which the changes in the wavelength based on the light reflection of an incident light as colored interference light brought about by changes in length or refractive index at the time the hybridization probe aligned in a film-like shape hybridizes with the target nucleic acid may be measured and examples include a method in which the changes in wavelength are measured using a spectrophotometer.

In accordance with the target nucleic acid detecting method of the present invention, the change in wavelength based on the reflection of the incident light as colored interference light brought out by changes in length or refractive index at the time the film-like hybridization probe hybridizes with a target nucleic acid is measured, it is now possible to quickly and surely detect the presence of the target nucleic acid by a simple operation.

EXAMPLES

As hereunder, the present invention will be more specifically illustrated by the following examples although the present invention is not limited to such examples.

Example 1

DNA chain having a K-ras mutation sequence having a sequence which is different only in one base from human normal chromosome K-ras gene was prepared using a pair of primers having a one-base mismatch from the following human normal chromosome K-ras gene.

k-ras-5 m (mutation base is underlined)

SEQ ID NO: 1

5'-TATAAACTTGTGGTAGTTGGACCT-3' k-ras-3

SEQ ID NO: 2

5'-TATCGTCAAGGCACTCTTGCC-3'

A gene amplifying reaction was carried out by a PCR method in a reaction solution containing 100 μl of 10 mM Tris-hydrochloride buffer (pH 8.3), 50 mM KCl, 1.5 mM $MgCl_2$, 0.001% gelatin and 2 units of Ampli taq™ DNA polymerase in the presence of 200 μM dNTP using Bio-k-ras-5 m (100 ng) into which biotin was introduced and Bio-k-ras-3 (100 ng) into which biotin was introduced as a pair of primers and using 100 ng of human normal chromosome K-ras gene as a template. In the PCR method, a Thermal Cycler PJ 2000 (manufactured by Perkin-Elmer) was used and a cycle of 94° C. for 30 seconds and 56° C. for 30 seconds was repeated for 35 times. The resulting reaction solution was analyzed by an agarose gel electrophoresis and its size and amplifying efficiency were measured.

Next, polymerization of $N^\epsilon$-carbobenzoxy L-lysine $N^\alpha$-carboxylic acid anhydride (LLZ-NCA) was carried out using n-hexylamine as an initiator and then polymerization of γ-methyl L-glutamate N-carboxylic acid anhydride (MLG-NCA) was carried out to prepare a block copolypeptide $PLLZ_{2000}$-$PMLG_{600}$ in which degree of polymerization of a PLLZ moiety was 2000 and that of a PMLG moiety was 600. After that, the PMLG segment was partially hydrolyzed to give L-glutamic acid (LGA) in which α-helix copolypeptide $PLLZ_{250}$-$P(MLG_{420}/LGA_{180})$ was prepared.

Avidin was introduced into this α-helix copolypeptide followed by bonding to biotin of the DNA chain having the K-ras mutation sequence in which a hybridization probe was prepared.

Then, the hybridization probe was kept in a state of being floated (horizontal state) on a water surface (aqueous phase) and pH of the water (aqueous phase) is made alkaline of around 12 in which the α-helix structure in the hydrophilic area of the probe is disentangled to give a random structure. At that time, the hydrophobic area of the probe still maintains its α-helix structure. Then, pH of the water (aqueous phase) is made acidic of around 5 in which the hydrophilic area in the probe forms an α-helix structure again. When the pushing material attached to the probe is pushed by the pressure of air from its side to the probe at that time, the probe is still in a state of being vertical to the water (aqueous phase) while its hydrophilic area forms an α-helix structure in the direction Substantially orthogonal against the surface of water in the aqueous phase. When the probe in an aligned state is pushed out onto the substrate (plate) using a pushing material as mentioned above, it is possible to form a monomolecular film in which the probe is vertically stood on the substrate (plate). Incidentally, this operation was carried out using an apparatus for forming a HYBRIDIZATION PROBE membrane (NL-LB 400NK-NWC; manufactured by Nippon Laser & Electronics Laboratories). Thickness of this monomolecular film was calculated to be about 16 nm.

The resulting substrate in which the hybridization probe was vertically stood in a state of a monomolecular film was aligned in a solvent containing K-ras mutation gene prepared from a cDNA library and changes in wavelength by the light reflection of an incident light as colored interference light were measured in which, as compared with the case in which addition was conducted to a solvent containing no K-ras mutation gene, significant changes in wavelength were observed.

Example 2

Monomolecular film in which a hybridization probe was vertically stood on a substrate (plate) in Example 1 was used as a structure unit comprising two layered monomolecular films to prepare a substrate in which the hybridization probe was vertically stood in a form of two layered monomolecular films. The substrate was aligned in a solvent containing K-ras mutation gene prepared from a cDNA library and the changes in wavelength based on the light reflection of an incident light as colored interference light were measured by a spectrophotometer in which, as compared with the case in which addition was conducted to a solvent containing no K-ras mutation gene, significant changes in wavelength were observed.

Example 3

A product in which a gold electrode having an area of 0.2 cm² and a gold-plated lead wire were attached to a quartz oscillator (AT cut; area: 0.5 cm²; basic frequency: 9 MHz) was used as a quartz oscillator electrode.

The quartz oscillation electrode was dipped at room temperature for 1 hour in a 1% by volume aqueous solution of aminopropyl triethoxysilane (manufactured by Chisso) and washed by irradiating with ultrasonic wave of 20 kHz in pure water for 30 minutes to remove an excessive aminopropyl triethoxysilane. After that, the quartz oscillation electrode was subjected to a thermal treatment for 20 minutes at the temperature of 110° C. whereby a covalent bond was formed between aminopropyl triethoxysilane and quartz oscillator surface.

Then this quartz oscillator was dipped for 1 hour in a 1% by volume aqueous solution of glutaraldehyde to form a covalent bond between glutaraldehyde and aminopropyl triethoxysilane and, after that, the quartz oscillator was washed by irradiating with ultrasonic wave of 20 kHz for 30 minutes in pure water to remove an excessive glutaraldehyde.

The quartz oscillator electrode was dipped for 2 hours in 100 ml of a phosphate buffer of pH 7.2 containing the hybridization probe prepared in Example 1. As a result thereof, the hybridization probe was fixed to the quartz oscillator via glutaraldehyde. The unreacted physical checkup medicament was removed by washing with a phosphate buffer of pH 7.2.

After that, the quartz oscillator prepared as such was attached to the target nucleic acid detecting apparatus shown in FIG. 8, then a predetermined amount of solvent containing K-ras mutation gene prepared from a cDNA library was added to a phosphate buffer and changes in frequency during 10 minutes were checked. Within one minute, the changes in the oscillation frequency almost reached saturation. The thing in which a solvent containing K-ras mutation gene was added showed a clear reduction in oscillation frequency as compared to those without.

When the adding amount of K-ras mutation gene increased, it was found that the oscillation frequency decreased in a certain rate.

Example 4

A target nucleic acid detecting apparatus was assembled in the same manner as in Example 3 except that, in place of the quartz oscillator in Example 3, there was used a surface acoustic wave (SAW) element of ST cut as shown in FIG. 9 in which oscillation frequency was 10.3 MHz.

To a phosphate buffer was added a predetermined amount of a solvent containing K-ras mutation gene prepared from a cDNA library and changes in oscillation frequency during 10 minutes were checked. Within one minute, the changes in the oscillation frequency almost reached saturation. In the sample in which a solvent containing K-ras mutation gene was added showed a clear reduction in oscillation frequency as compared to those without added.

When the adding amount of K-ras mutation gene increased, it was found that the oscillation frequency decreased in certain rate.

In accordance with the present invention, the formation reaction of DNA hybrid may be directly manifested in aqueous phase or gaseous phase without special technique within a short time and, at the same time, formation of DNA hybrid may be tested easily and highly precisely. In addition, the hybrid formation may be quantitatively tested if necessary.

What is claimed is:

1. A hybridization probe comprising,
   a helical organic molecule having a length of 810 nm or shorter which is aligned to form a film, wherein said helical organic molecule is not DNA; and
   a polynucleotide bonded to the helical organic molecule wherein said polynucleotide hybridizes to a target polynucleotide, and
   wherein the film reflects incident light as a colored interference light, thereby allowing detection of the target polynucleotide by detecting a change in color of the colored interference light.

2. The hybridization probe according to claim 1, wherein the polynucleotide is RNA or single-stranded DNA.

3. The hybridization probe according to claim 1, wherein the target polynucleotide is selected from the group consisting of:
   a) a prokaryotic polynucleotide;
   b) a eukaryotic, non-human polynucleotide; and
   c) a polynucleotide that exists only in a human.

4. The hybridization probe according to claim 1, wherein the target polynucleotide is selected from the group consisting of a cancer-related gene, a gene related to a genetic disease, a virogene, a bacterial gene and a gene having a polymorphism that is a risk factor for a disease.

5. The hybridization probe according to claim 1, wherein presence of the target polynucleotide indicates a presence of a second target polynucleotide.

6. The hybridization probe according to claim 1, wherein the hybridization probe is amphiphilic.

7. The hybridization probe according to claim 1, wherein the helical organic molecule is selected from the group consisting of an α-helix polypeptide and amylase.

8. The hybridization probe according to claim 7, wherein the hybridization probe is amphiphilic.

9. The hybridization probe according to claim 8, wherein the helical organic molecule is a block polymer of α-helix polypeptide.

10. The hybridization probe according to claim 1, wherein the hybridization probe is amphiphilic.

11. A target polynucleotide detecting kit comprising:
    a hybridization probe; and
    any one of a dish, plate or tube;
    wherein the hybridization probe comprises a helical organic molecule, and a polynucleotide bonded to the helical organic molecule; wherein the helical organic molecule is not DNA, and wherein the helical organic molecule has a length of 810 nm or shorter which is aligned to form a film, wherein the polynucleotide hybridizes to a target polynucleotide, and wherein the film reflects incident light as colored interference light, thereby allowing detection of the target polynucleotide by detecting a change in color of the colored interference light.

* * * * *